(12) United States Patent
Takaleh

(10) Patent No.: US 9,277,799 B2
(45) Date of Patent: Mar. 8, 2016

(54) HENNA APPLICATOR DEVICE AND A METHOD OF OPERATING THE SAME

(71) Applicant: United Arab Emirates University, Al Ain (AE)

(72) Inventor: Effat Takaleh, Al Ain (AE)

(73) Assignee: United Arab Emirates University, Al Ain, (AE)

( * ) Notice: Subject to any disclaimer, the term of this patent is extended or adjusted under 35 U.S.C. 154(b) by 0 days.

(21) Appl. No.: 14/256,821

(22) Filed: Apr. 18, 2014

(65) Prior Publication Data

US 2015/0296959 A1   Oct. 22, 2015

(51) Int. Cl.
*B41J 3/00* (2006.01)
*A45D 40/26* (2006.01)
*A61Q 1/02* (2006.01)

(52) U.S. Cl.
CPC ............... *A45D 40/26* (2013.01); *A61Q 1/025* (2013.01)

(58) Field of Classification Search
None
See application file for complete search history.

(56) References Cited

U.S. PATENT DOCUMENTS

| | | |
|---|---|---|
| 5,268,166 A | 12/1993 | Barnett et al. |
| 6,341,831 B1 | 1/2002 | Weber et al. |
| 7,648,364 B2 * | 1/2010 | Dauga ................ A45D 44/005 434/100 |
| 8,036,448 B2 | 10/2011 | Gildenberg |
| 2002/0155069 A1 | 10/2002 | Pruche et al. |

FOREIGN PATENT DOCUMENTS

| | | |
|---|---|---|
| CN | 1486852 A | 4/2004 |
| DE | 202007007308 U1 | 10/2007 |
| JP | 2002019087 A | 1/2002 |

OTHER PUBLICATIONS

International Search Report, International Patent Application No. PCT/IB2015/052842, dated Jun. 22, 2015, 4 pages.
Written Opinion, International Patent Application No. PCT/IB2015/052842, dated Jun. 22, 2015, 5 pages.

* cited by examiner

*Primary Examiner* — Lisa M Solomon
(74) *Attorney, Agent, or Firm* — Fitch, Even, Tabin & Flannery LLP

(57) ABSTRACT

The present invention relates to a system for applying a coloring substance preferably henna on at least one surface of the human body. The device comprises a scanning device configured to scan the body surface and detect movements of the body surface, a color applicator unit to apply the coloring substance onto at least one surface of human body and the controller to coordinate the scanning device and the color applicator unit to work cooperatively to ensure that an accurate replica of the desired design is formed on the surface of the human body. The system has an added advantage of being able to halt the color application process on detecting the displacement of the body surface during the color application process.

24 Claims, 3 Drawing Sheets

HENNA APPLICATOR DEVICE AND A METHOD OF OPERATING THE SAME

FIELD OF THE PRESENT INVENTION

The present invention relates to a system and method for applying a coloring substance on at least one surface of the human body with enhanced replication accuracy.

BACKGROUND

Since ancient times, the application of henna has been an important part of many religious customs and traditions. These traditions are widely regarded amongst the Middle Eastern, Indian and North African communities. More recently countries like US and Europe are adopting the culture of applying body tattoos as part of their latest fashion trends.

Body tattoos can be either a permanent or a temporary tattoo. Permanent tattoos are made by piercing the skin with a coloring substance such that coloring substance penetrates underneath the epidermis. If at a later stage a person desires to change the tattoo or to remove it permanently, the remedy is a Q-switched laser surgery or other skin abrasive techniques which are not only painful but also expensive. It is thus preferable to apply a semi-permanent tattoo which will fade off eventually and can be easily replaced by a new tattoo as desired.

Traditionally semi-permanent coloring substances like henna and carmine are manually applied on the body surface by a professional. In this process, the professional puts the coloring substance in a cone shaped plastic container wherein the broad end of the cone shaped plastic container is sealed and a small opening is made on its tapering side. The professional then applies the coloring substance onto the skin of the user by pressing the sealed end of the cone shaped plastic container using his fingers. On pressing the sealed end, a string of coloring matter is released from the small opening which is then laid carefully onto the skin of the user for creating different design patterns. It is imperative that the string of coloring substance be carefully laid on the skin as the moment the coloring string touches the skin surface, it imparts color to the skin surface. Thus any mistake made during the color application phase will result in the formation of a disrupted pattern. Also, there is a possibility that while applying the coloring substance the professional may accidently move his hand or apply more pressure on the cone shaped plastic container, which can further result in disrupted pattern or color patches on the skin surface. Hence it is necessary to apply the coloring substance correctly in the first instance. When using a plastic cone for applying the coloring substance, there is also a possibility that the thickness of the color string may not be uniform, the design orientation may not be accurate, the professional applying henna might get tired drawing elaborate patterns which in turn leads to the unpredictability of replication of the desired design.

If the design pattern is intricate and artistic in nature, then the time required for applying the coloring substance by the professional will be very high. In this modern age, time is of the essence, so it is a necessity to device a system and method which can enable the application of the coloring substance on the skin surface in a fast, reliable, less time-consuming and economic manner.

Various types of devices are known in prior art to enable the application of a coloring substance directly onto the skin surface. U.S. Pat. No. 5,268,166 describes a method of applying a coloring substance onto a skin surface by means of electrostatic spraying. US Patent Application 2002/0155069 refers to the application of the coloring substance on a localized skin surface in a predetermined design. However, various such devices suffer from one or more limitations as will be explained below.

It is imperative to hold the skin surface steady till the time the color application process is completed. The time consumed during the color application process may vary depending on the selected design. For more elaborate design, time required to replicate on the body surface is high. For an individual, it is difficult to hold the hand steady for extended periods of time. In both of the above mentioned prior art documents, there are no provisions for detecting any movements of the skin surface nor to halt the color application process on detecting movement of the skin surface till the time the individual is ready to resume the color application process.

It is thus an object of the present invention to address the problems faced by people wishing to apply a coloring substance on their skin surface by providing a system that can replicate any desired pattern on the skin surface of the user with enhanced replication accuracy and make the entire experience of applying the coloring substance more enjoyable by consuming less time and being economic in nature.

SUMMARY

An object of the present invention is to provide a system and a method for applying a coloring substance on at least one surface of the human body.

The expression "surface of the human body" relates to a body surface selected from a group comprising of the skin of the arms, hands, fingers, legs and toes. In a preferred embodiment, the body surface relates to the skin of the arms, hands and fingers.

As an aspect of the invention, there is provided a system for applying a coloring substance on at least one surface of the human body, said system comprising, a color applicator unit, a scanning device, an axle assembly and a controller.

The color applicator unit is configured to apply a coloring substance on at least one body surface. The scanning device is coupled to the color applicator unit and is configured to scan at least one body surface. The axle assembly is coupled to the color applicator unit and the scanning device and is configured to allow the movement of the coupled devices in one or more axis relative to at least one body surface. The controller comprises a memory system, a data processing unit and a control unit and is configured to enable the process of applying a coloring substance on the body surface by coupling the function and movement of the color application unit, scanning device on the axle assembly.

The system further comprises a user interface configured to select a design to be replicated on the body surface, modify the selected design and view it relative to the body surface.

The system comprises at least one scanning device. In a preferred embodiment, the system of the invention comprises three types of scanning devices to carry out the three functions: a) to scan the profile and the thickness of the body surface, b) to detect the movements in the body surface while applying a coloring substance, and c) to detect the distance between the color applicator unit and the body surface. The three scanning devices to carry out the functions a), b) and c) mentioned above are scanner sensor, displacement scanner and proximity scanner respectively. In a preferred embodiment, the three scanning devices are incorporated into a single scanning device of the invention.

In another preferred embodiment, the system is configured to stop applying the coloring substance on the body surface on detecting movement of the body surface during the color application process.

Once, the process of applying coloring substance on the body surface has paused, it can be resumed only after the user manually resumes the process by selecting "continue color application" on the user interface.

The system after resuming the process of color application re-scans the entire length of the body surface, and begins to apply the coloring substance on the body surface from the exact position where it had initially halted as a result of displacement of the body surface.

Another aspect of the invention is a method for applying a coloring substance on the body surface in a desired design using the system of the invention.

The method of applying a coloring substance on the body surface comprises the following steps: a) selecting a design from the memory of the system using an user interface, b) obtaining images of the body surface using a scanning device, c) processing the images to determine the position coordinates of the scanning device and the color applicator unit on the axle assembly, d) positioning the scanning device and the color applicator unit on the axle assembly using a control unit, e) applying a coloring substance on body surface by precision control action of the controller.

The method further comprises detecting movement of the body surface during the color application process using the displacement sensor. The system is capable of halting the color application process if the displacement as detected by the displacement sensor exceeds a threshold value of from 0.15 and 0.35, preferably the displacement threshold value is 0.25 mm.

Once the displacement has been detected, the color application process halts midway and the system may only resume the color application process after inputting through the user interface instructions to resume the color application process.

After resuming the color application process, the scanning device rescans the body surface and sends signals to the data processing unit to determine the position where the color application process had halted and after determining the position coordinates, it directs the control unit to position the color applicator unit over the body surface to resume the application of the coloring substance from the exact position where it had halted.

In a preferred embodiment, the system of the inventions starts applying the coloring substance on the arm and moves towards the fingers when the body surface is the hand of the user or the system applies the coloring substance starting from the ankle and moves towards the toes when the body surface is the leg of the user The system is further configured to apply multiple layers of the coloring substance on the body surface to create a thick design pattern.

The term "coloring substance" refers to any substance with an ability to impart color to a surface. The substance can refer to any color, ink, dye, stain, pigment or any mixtures thereof. Various types of coloring substance can be used for application on the body surface using the present invention. Coloring substance is chosen from a list comprising henna, turmeric, parsley, paprika, alkanet root, carmine, annatto seed, sandalwood and saffron. Also chemical coloring agents can be used.

By using the system and method of the present invention, a user may be able to replicate any desired design pattern on the body surface of the user with enhanced replication accuracy.

BRIEF DESCRIPTION OF THE DRAWINGS

The accompanying drawings, which are in incorporated into and form part of this disclosure, illustrate embodiments of the present invention and together with the description, serve to explain the techniques of the present invention.

DETAILED DESCRIPTION

Figure 1:
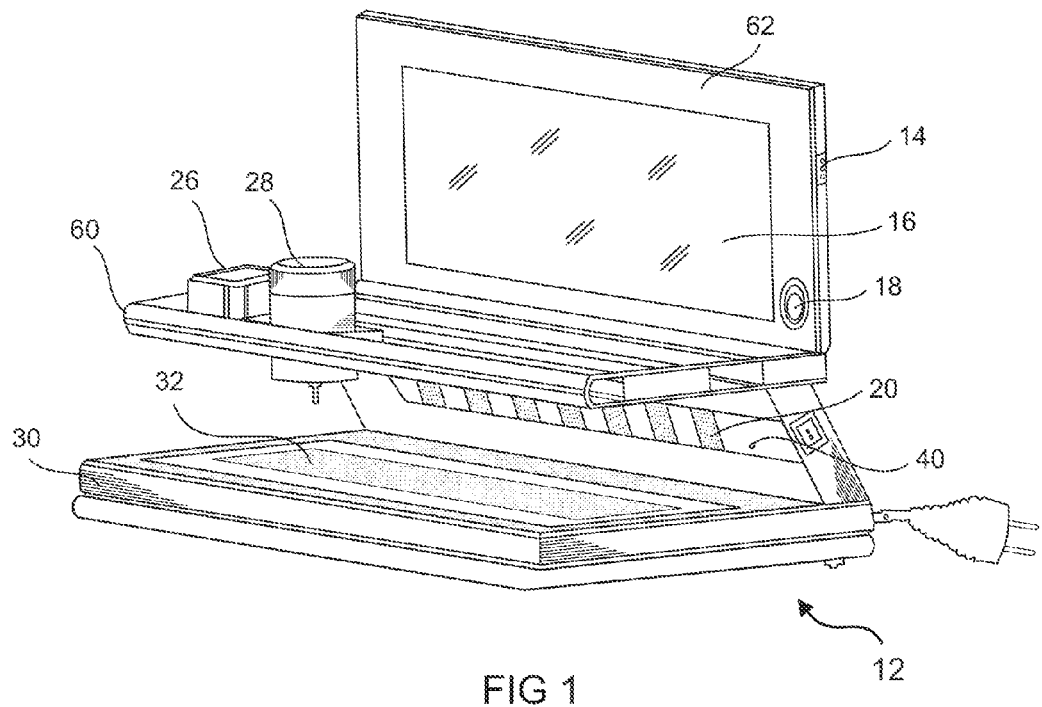
FIG. 1 is a detailed view of the present invention according to one embodiment of the present invention.

According to the broadest aspect, the present invention relates to a system and a method for applying a coloring substance on the body surface. The system of the present invention comprises a scanning device, a color applicator unit and an axle assembly wherein, the scanning device is configured to scan the body surface, the color applicator unit is configured to apply the coloring substance on the body surface and the movement assembly is configured to move the color applicator unit and the scanning device relative to the body surface during the color application process.

The system further comprises an applicator base, over which the body surface is placed during the color application process, a memory system to store the design patterns, a user interface comprising a display unit, preferably a touch screen display unit enabled to select the design and view it relative to the body surface, a data processing unit configured to analyze and process the signals, images and data obtained from the scanning device, user interface and the displacement sensor device and a control unit enabled to convert the digital signals obtained from the data processing unit into mechanical movements to enable the color application process. The system further comprises a communications unit which acts as a medium for transfer of instructions and signals between the different components of the system of the present invention.

In a preferred embodiment, the memory system, the data processing unit, communications unit and the control unit may be present as part of a single system called the controller. The controller is a microprocessor unit which contains the memory system, data processing unit, communications unit and the control unit present system integrated into a single component.

The memory system is typically configured to store images, designs and the requisite software programs to enable the color application process. The memory system includes conventional storage devices such as Random Access Memory (RAM), Read-Only Memory (ROM) incorporated into the controller. Also, external memory devices may be connected to the said system. The external memory devices comprise memory chips, flash memory/drives and hard disks. Also, an external CD ROM and Floppy disk can be connected to the system by means of an adaptor cable.

The data processing unit may be configured to receive signals and images from the scanning device and the user interface. The data processing unit transforms the signals and images in a form readable by the control unit to perform the color application process. The data processing unit can be selected from a list comprising central processing unit (CPU), microprocessor and "computer on chip" devices.

The communications unit is configured to exchange data and instructions between different components of the system including the scanning device, the memory system, the user interface, the data processing unit and the control unit.

The control unit is generally enabled to perform the mechanical operations such as the movement of the color applicator unit, scanning device and displacement sensor device on the movement assembly and applying a coloring substance on the body surface.

The present invention further relates to a method of applying a coloring substance on the body surface of the user, the method comprising selecting a design intended to be replicated on the body surface, scanning the body surface on which the user intends to replicate the design pattern, and applying the coloring substance on the body surface in the desired pattern using the system of the invention.

The method further comprises detecting the displacement of the body surface during the color application process. The apparatus performing the detection of the body surface displacement is the displacement sensor. The major advantage of the system of the present invention is that once a movement of the body surface is detected, the color application process is halted till the time the user manually resumes the color application process.

The user intending to apply a coloring substance on the body surface first switches on the device using the power button provided on the user interface and selects a design pattern.

The user interface comprises a display unit for interaction, a power switch to start the device and a connector configured to connect the system to external devices. The power switch can be switched on by simply touching the power sign on the display unit. A modification of the system can be provided by the use of a remote control, a rocker or toggle switch to start the system. The external devices may comprise external memory systems, data processing devices and digital drawing pads.

In a preferred embodiment, the display unit used is a touch screen display unit. In lieu of a touch screen display unit, a regular display screen can be provided with buttons present on either sides of the regular display screen to provide an interactive system. Another modification makes use of a keyboard. A further modification can be incorporated by enabling the operation of the device from a short line-of-sight distance by the use of a remote control. This remote control may be either affixed to the display screen by means of a cable or may be used wirelessly from a short distance. A further modification of the system comprises the incorporation of voice control system and motion-sensor enabled capabilities.

The design pattern or simply called design is any combination comprising lines, curves and diagrams in a fixed pattern. This design may be selected from the memory of the system or can be uploaded into the memory using digital data storage mediums. A connector is provided on the user interface to upload the designs. The connector is used to connect to external data storage devices by means of a plug. The external storage devices comprise flash drives, hard disks, camera, mobile phones, CD ROM and floppy discs. Any design may be uploaded into the memory of the system provided it is in a format readable by the data processing unit.

After the user selects the design on the touch screen display unit, the user places the body surface intended for the color application process on the applicator base. In a preferred embodiment, the body surface is the arm, hand and fingers of the user.

The scanning device then scans the entire length of the arm, hand and fingers. The scanning device contains a central scanning lens and 2 sockets. The first socket is a connector socket that links the scanning device to the data processing unit and the control unit by means of the communications unit. The second socket is a power socket used for connecting the scanning device to a power plug. The central scanning lens is configured obtain images of the body surface on which the coloring substance is to be applied.

Various types of scanning devices may be incorporated into the said system. The scanning device may be selected from Micro-Epsilon®, LJ-V7000® from Keyence, Profile scanner 59132® by Hamamatsu, LPS® by Leuze Electronics and Photo Electric Sensors from Baumer and UTM-0LX. The scanning device preferably possesses at least a 2D planar laser scan and at least 270° field of view. In a preferred embodiment, the scanning device utilizes a triangulation-type displacement sensor.

The images obtained from the scanning device are viewable on the touch screen display unit in the form of 3-Dimensional (3D) images. The data processing unit of the controller receives the images from the scanning device via the communications unit and displays it on the touch screen display unit in the form of a 3D image superimposed with the selected design. The user is now able to view the selected design relative to the body surface. At this point the user may choose to continue with the color application process or can reselect another design. If the user reselects the design, the scanning device rescans the entire length of the arm and the data processing unit further regenerates a 3D image of the arm superimposed with the new design.

The system also contains a program configured to modify the selected design. The modification comprises cropping the image, rotating the image, and resizing the image. This gives the user the advantage of customizing the selected design as it suits the user's requirements. The program used for performing such modifications is similar in function to digital programs like Adobe Photoshop, Microsoft Paint, Coral Design and Picassa tools. There is also present a software to enable the user to draw its own design using a stylus. Using the stylus, the user can draw the design directly onto the touch screen display unit and save it into the memory of the system. In addition, an external digital drawing pad may be attached to the said system using the connector.

Once the user finalizes the design, the system prompts the user to select the "continue color application" option displayed on the touch screen display unit. After the user selects the "continue color application" option, the controller positions the color applicator unit over the body surface on the axle assembly. A string of coloring substance is then released from the material holding container onto the body surface. During the color application process, the color applicator unit moves along the body surface to create an exact replica of the selected design on the body surface using the coloring substance.

The color applicator unit comprises a material holding container, a material dispenser nozzle, a lid and a piston-type device. The material holding container helps to store the coloring substance during the color application process. The material dispenser nozzle comprises an applicator needle with a diameter in the range of from 0.5 mm to 1.5 mm. The applicator needle towards the end facing the body surface is fitted with a rubber tip. The rubber tip prevents the applicator needle from pricking the body surface during the color application process. At the intersection of the lid and the material holding container a rubber seal is present to ensure that the coloring substance present inside the material holding container remains air-tight and moisture-tight.

In the present invention, the color applicator unit is coupled to the scanning device. Therefore, during the color application process, the scanning device moves with the color applicator unit on the axle assembly relative to the body surface by means of sliding interlocks incorporating sliding gear mechanisms.

The color applicator unit and scanning device moves over the body surface in three axes. This movement is brought about by means of two axles. One axle is spread on the length of the system and enables the movement of the color applicator unit and the scanning device in the x-axis. The second axle is a square frame axle that holds the color applicator unit and the scanning device and allows the movement in the y and z axis. The movement of the color applicator unit and the scanning device is similar to the ink jet printer, wherein there is one major axle that allows the movement along the device in the x axis, and the minor axle which is the square frame axis that holds the color applicator unit and enables its movement the y and z axis. These two axles form the axle assembly and enable the color applicator unit and the scanning device to move faster and smoother owing to the simpler design and decrease in the friction between the axle and the sliding gear mechanism.

During the color application process, the movement of the color applicator unit and the scanning device is determined on the basis of the design selected by the user. After the user selects the design, the data processing unit analyses and processes the design and stores it in a first reference coordinate system. The image of the body surface captured by the scanning device is analysed and processed by the data processing unit and stored in a second reference coordinate system. After the user selects "continue color application", the data processing unit correlates the first and second reference coordinate systems and generates a third reference coordinate system. This third reference coordinate system is used by the control unit to position the color applicator unit and scanning device on the axle assembly relative to the body surface. This is the first/starting position. The third reference coordinate system helps to determine the x-axis and y-axis position coordinates of the applicator needle.

The scanning device is also configured to obtain real time images of the body surface during the color application process by means of a proximity sensor. The real time images help to assess the topographical features of the body surface. The topographical features include the height, length, width and other surface related features of the body surface. The data processing unit processes the real time images and signals obtained from the scanning device and compute the distance between the body surface and the applicator needle. The data processing unit then calculates the distance between the applicator needle and the body surface maintaining the minimum gap in the range of from about 1.5 mm to 5 mm between the body surface and the applicator needle. This distance helps to determine the reference coordinates for movement of the color applicator unit and the scanning device in the z-axis. At any point of time, during the color application process, the distance between the tip of the applicator needle and the body surface is maintained in the range of from about 1.5 mm to 5 mm. In a preferred embodiment, during the color application process, the applicator needle is positioned not less than 2 mm above the body surface.

During the color application process, the control unit exerts a predetermined amount of pressure on the coloring substance present inside the material holding container using a piston-type device. Due to this pressure, a string of coloring substance is released from the tip of the applicator needle. This string of coloring substance is laid on the body surface of the user based on the x-y-z axis coordinates obtained from the data processing unit.

During the color application process, the applicator needle lays a single string of coloring substance with the thickness of between 1.5 mm to 3 mm on the body surface of the user. The color applicator unit moves on the axle assembly relative to the body surface to apply a single layer of coloring substance on the body surface. After the color applicator unit completes applying a single layer of coloring substance on the entire body surface, in accordance with the selected design, the color applicator unit returns back to the first position. Over the regions wherein a thicker layer of the coloring substance is required, the color applicator unit starts reapplying a second layer of the coloring substance. The color applicator unit is configured to lay on the body surface multiple layers of coloring substance until the selected design is replicated in entirety on the body surface of the user.

If during the color application process, the applicator needle accidently pricks the body surface, the color application process must be immediately halted and the applicator needle sterilized prior to next usage. The applicator needle may be sterilized using any of the techniques comprising heat sterilization, chemical sterilization and irradiation, and any combinations thereof.

During the color application process, it is desired to hold the body surface steady till the time the color application process has successfully completed. To help maintain the body surface steady, there is provided a grip tape on the applicator base. The body surface on which the color has to be applied is kept over the grip tape to provide resistance to minor body movements. Further modifications can be incorporated into the system by building a cage-like structure into which the body surface of the user is placed. This cage-like structure will preferably restrict small body surface movements of the user during the color application process.

The system further comprises displacement sensors. These displacement sensors are configured to detect any movements of the body surface during the color application process. The displacement sensors can be chosen from PIR sensors that can sense any movement of the body surface of the user including but not limited to arm, hand, fingers, leg, foot and toes. The displacement sensor is preferably incorporated into the scanning device.

During the color application process, the displacement sensor continuously monitors for any movements of the body surface. The data processing unit receives processes and analyses the signals obtained from the displacement sensor. If the data processing unit detects a movement of the body surface greater than 0.25 mm, the data processing unit signals to the control unit to halt the color application process.

The role of the displacement sensor is to obtain images from the camera loaded therein in real time. These images are sent to the data-processing unit wherein the images are analyzed. During analysis, the data processing unit generates an outline of the hand and translates it into software. If there are significant differences between the sequential images, the data processing unit signals to the control unit to halt the color application process.

Once the color application process is halted, the system performs the following functions: a) the control unit stops the piston-type device to apply pressure on the color holding container and b) the color applicator unit and the scanning device are returned to the starting position.

The user is also able to manually halt the color application process by selecting the "pause color application" via the user interface.

On halting the color application process, the system prompts the user to resume the color application process via the user interface. The user is required to manually select "resume application" on the user interface and lay the body surface on the applicator base.

On resuming the color application process, the scanning device re-scans the entire length of the body surface. Based on the signals received from the scanning device, the data processing unit now generates a fourth reference coordinate system. The fourth reference coordinate system represents the coordinates relating to the position wherein the color application process had initially halted. The data processing unit then directs the control unit to re-position and re-direct the color applicator unit to resume the color application process from the exact position where the color application process had halted.

The system further comprises fans to dry the coloring substance on the body surface. These fans are present on the slanted assembly. The slanted assembly forms a connecting link between the user interface, movement assembly and the applicator base. It is so named as the assembly is arranged at an angle of from 120° and 140°. The slanted assembly comprises plurality of fans. About 5-10 fans can be incorporated into the slanted assembly.

After the design is imprinted on the body surface, the system prompts the user to switch on the fans to enable drying the coloring substance on the body surface. The user may switch on the fans by means of a rocker switch provided on the slanted assembly.

Once the coloring substance has dried, the user may remove the body surface from the applicator base. The user may further choose to apply the coloring substance on other body surfaces. If not, the system may be switched off.

Once the system is switched off, the remaining coloring substance should be removed from the material holding container and the material holding container and the needle should be washed, dried and replaced on the system for later use.

The system of the present invention can be enabled using PIR sensors of motion that senses any motion of the body surface, a scanner sensor that scans the profile of the body surface and its thickness. These two sensors are connected with Arduino Uno which is the brain chip that translates signals and orders from sensors to the software. Other controllers used that are connected to the Arduino UNO are electric servos that allows the motion of the axles that hold the color applicator unit. The Arduino UNO used is the Arduino UNO board. Other sensors that may be used include but are not limit to rf receivers, distance sensor, light sensor and force sensing sensor A software program is designed and installed into the system to carry out the color application process using the system of the invention. The software program performs the functions of a) prompting the user to select design; b) signaling to the scanning device to obtain images; c) processing the selected design and images from the scanning device; d) prompting the user to confirm the selection and orientation of the design relative to the body surface; e) directing the color applicator unit to apply the coloring substance on the body surface; and f) halting the color application process if necessary as and when a movement of body surface is detected. It should be noted that while specific examples of a controller device and a software program have been mentioned above only by way of example and it should not be construed to limit the present invention in any manner whatsoever.

Further modifications to the system can be incorporated to include sensors to indicate whether the material holding container is empty or requires refilling, whether the applicator needle is blocked and whether there is friction during movement of the scanning device and the color applicator unit on the axle assembly.

The system of the present invention can further comprise a light source directed towards the body surface to provide a bright image of the body surface onto which the coloring substance is to be applied. The light source may be coupled to the scanning device and configured to move with the scanning device and the color applicator unit during the color application process. Although any light source may be used, it is preferable to have a light source of low intensity.

The system of the present invention may further comprise a sensor to monitor the coloring substance being pumped from the applicator needle. In a preferred embodiment, the coloring substance being released from the applicator needle is in the form of a string. The string form of the coloring substance is manageable and can be easily laid on the body surface. The sensor will be able to determine the flow characteristics of the coloring substance and will accordingly signal to the data processing unit. The data processing unit will analyze the signal and correspondingly alter the pressure exerted by the piston-type device on the coloring substance present within the material holding container.

The figures are now described in detail as preferred embodiments of the present invention.

In a preferred embodiment, the system for applying a coloring substance on at least one surface of the human body is a system for applying henna on the arms, hands and fingers of the user. For ease of reference, the system of the invention is hereafter referred to as henna applicator device. However, it will be clear to those of skill in the art that the embodiments described could be used with other coloring substances.

Figure 2:
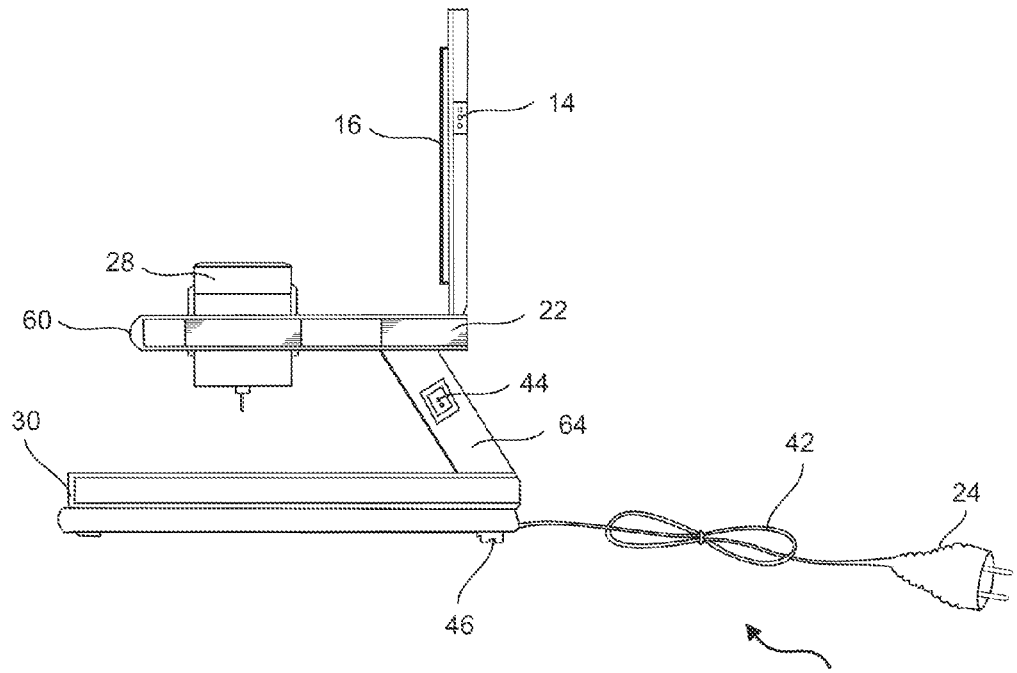
FIG. 2 shows a side view of the present invention.

According to one embodiment of the present invention, as seen in FIGS. 1 and 2, the henna applicator device of the present invention 12 comprises a user interface, a scanning device 26, a color applicator unit 28, a displacement sensor, an applicator base 30 and a controller. In a preferred embodiment, the scanning device 26 and the displacement sensor are the same.

The user interface comprises a touch screen display unit 16 fitted into the touch screen support board 62. The touch screen display unit 16 enables viewing the design and the body surface as well as provides a medium for interaction between the user and the henna applicator device. A power switch 18 and a connector 14 are present on the touch screen support board 62. The power switch 18 is preferably a toggle based switch. The connector 14 is present on the lateral side of the touch screen board 16. The connector 14 can be optionally used to connect the henna applicator device with external devices. External devices comprises external memory devices, processors, controllers and drawing devices.

The scanning device 26 is coupled to the color applicator unit 28.

Figure 3:
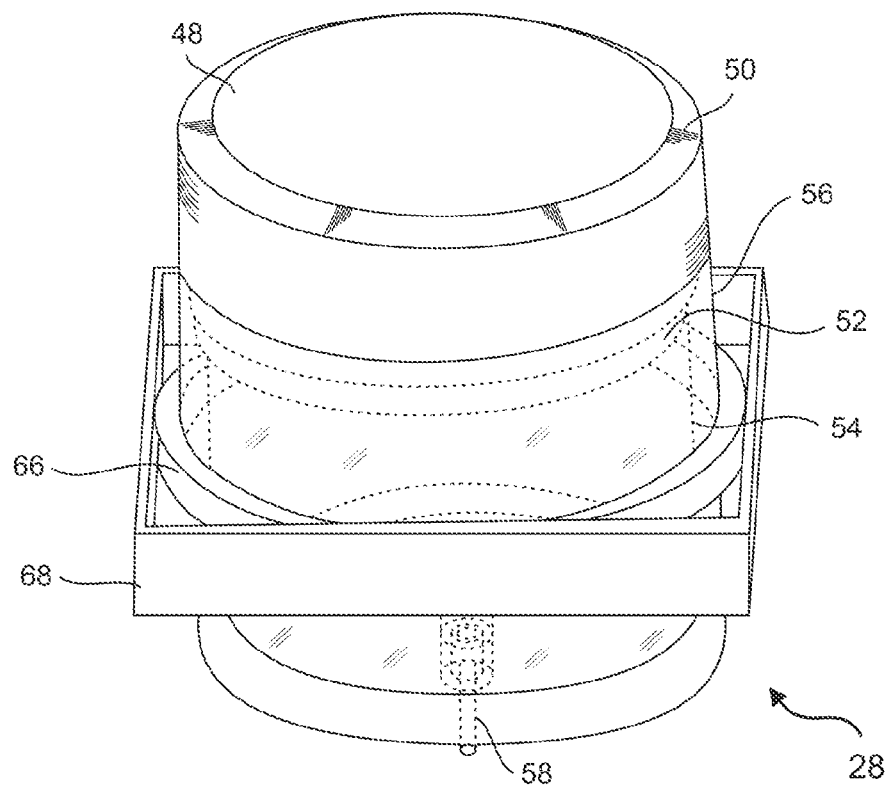
FIG. 3 is a diagrammatic representation of the color applicator unit.

A reference is made to FIG. 3 which illustrates the color applicator unit 28 in more detail. The color applicator unit 28 comprises a material holding container 54, an applicator needle 58 and a lid 48. The material holding container 54 is used for storing and dispensing henna during the color application process. The material holding container 54 is preferably a cylindrical container with a non-stick coating on the side facing the interior of the material holding container. The material holding container 54 is present inside a plastic casing 56. There is present a hoop 66 circling the outer side of the plastic casing 56. The hoop 66 is connected to a frame pole, also referred to as an axle. This axle forms a part of the axle assembly 60 and helps in the movement of the color applicator unit in the y and z axis.

A lid 48 is present on the upper side of the material holding container 52. The lid 48 is sealed to the material holding container 52 by means of a rubber seal 50. The rubber seal 50 renders the material holding container 52 air-tight and moisture-tight. The applicator needle 58 is located on the side opposite to the lid 48. The applicator needle 58 is hollow with a diameter in the range of from 0-5 mm-1.5 mm. The applicator needle 58 is fitted with a rubber covering at the tip on the side facing the applicator base to prevent pricking the arm of the user during the color application process. There is present a piston-type device 52 within the material holding container 54. The piston-type device 52 is configured to apply a predetermined amount of pressure, preferably about 952.2215 Pa, on the coloring substance present within the material holding container 52 such that a string of henna is released from the open tip of the applicator needle 58 during the color application process.

Figure 4:
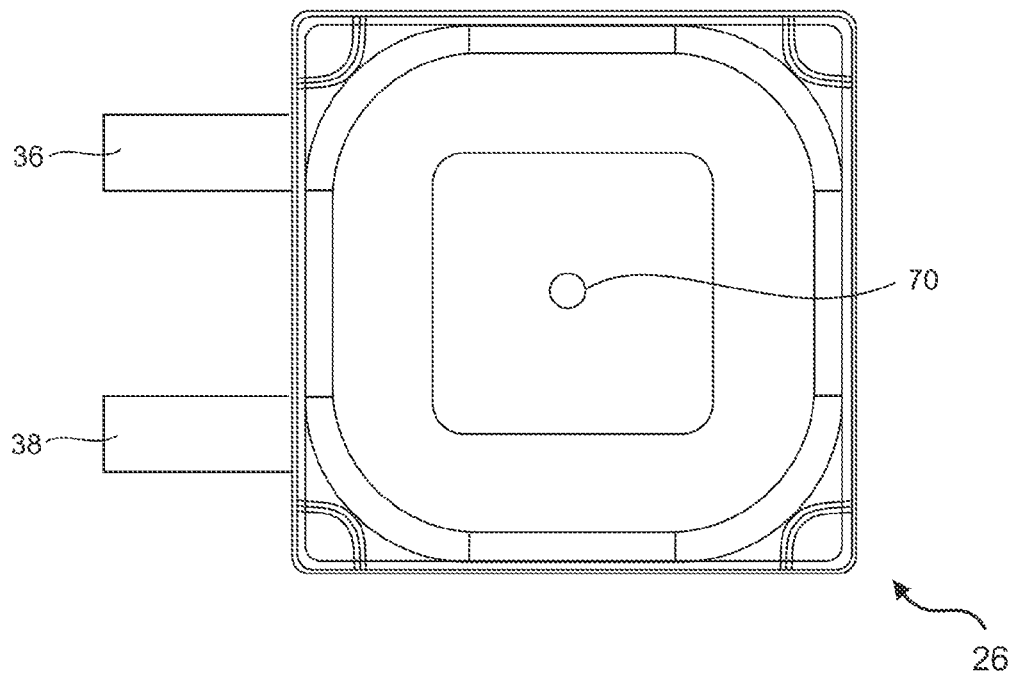
FIG. 4 is a diagrammatic representation of the scanning device.
Figure 5:
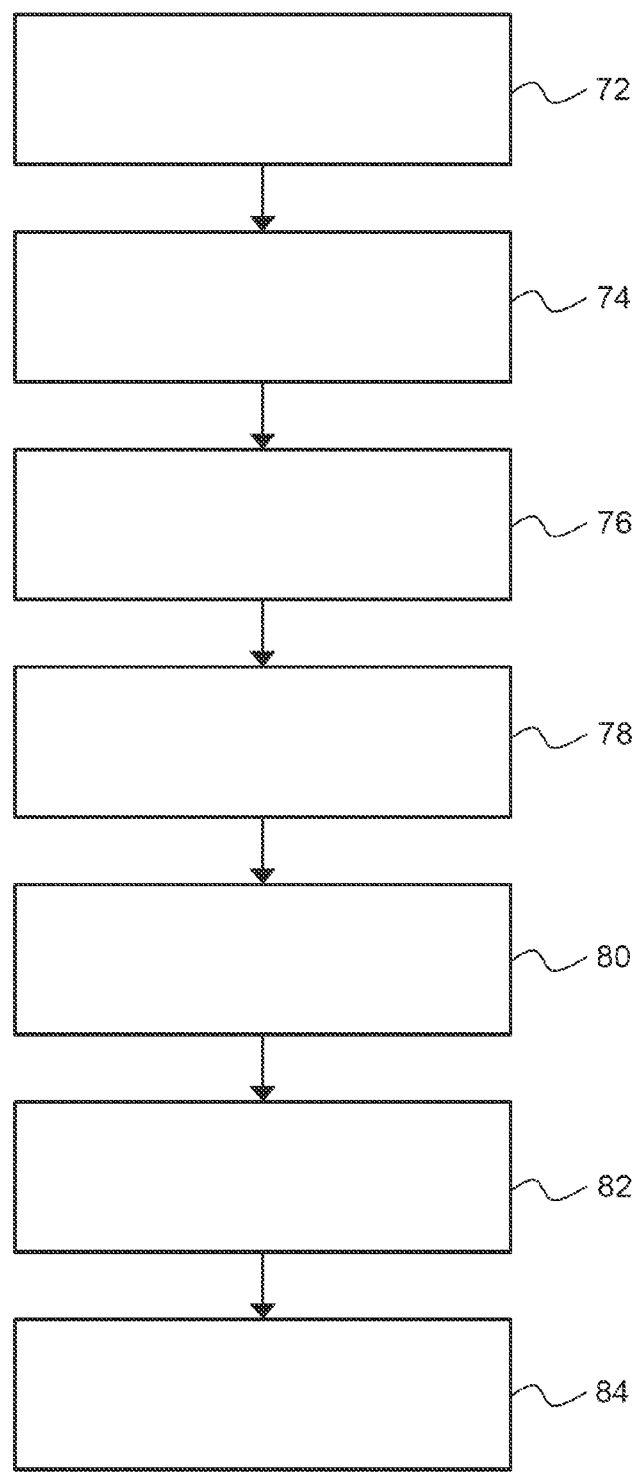
FIG. 5 is a flow chart representing the method for applying a coloring substance on a body surface.

Further reference is made to FIG. 4 which illustrates the scanning device 26 in detail. The scanning device 26 contains a central scanning lens 70, a connector socket 36 and a second socket 38. The connector socket 36 is configured to connect the scanning device 26 to the controller. The second socket is used to connect the scanning device to the power plug. The central scanning lens 70 is configured to perform a list of functions, said list comprising a) obtaining images of the body surface on which the color has to be applied; b) obtaining images of the body surface to determine the relative distance between the applicator needle and the body surface, during the color application process, and c) detecting movements of the body surface during the color application process.

The scanning device 26 is connected to the color applicator unit 28 at the frame pole. The scanning device 26 and the color applicator unit 28 are configured to move on the axle assembly 60 by the use of sliding interlocks. The sliding interlocks enable smooth movement of the scanning device and the color applicator unit on the axle assembly 60. The axle assembly 60 comprises at least two axles to enable the movement of the scanning device and the color applicator unit in at least three axis. The axle assembly 60 is fitted horizontally onto the touch screen board 62. The axle assembly 60 consists of the frame pole and a second axle which enables the movement of the color applicator unit and the scanning device in x, y and z axis.

A side connector 22 is present which runs parallel to the axle assembly 60. The side connector 22 forms a link between the touch screen board 62 and the slanted assembly 64. The side connector 22 further connects to the applicator base 30 by means of the slanted assembly 64.

The slanted assembly 64 is so named as it connects the applicator base 30 and the side connector 22 at an angle in the range of from about 120° to 140°. In a preferred embodiment, the side connector is present at an angle of about 137.66°. The slanted assembly 64 comprises plurality of fans 20. About 5-10 fans 20 can be incorporated into the slanted assembly 64. A plurality of fan units is first encased in a horizontal frame 40. The horizontal frame 40 is further encased in the slanted assembly 64. The slanted assembly 64 is fitted with a rocker switch 44 at any one of the lateral sides. The rocker switch 44 is used to switch on the fans 20 to enable drying of the coloring substance.

The slanted assembly 64 is connected with the applicator base 30 on its bottom side. The applicator base 30 comprises a flat applicator surface. On the top side of the application surface, there is provided a grip tape 32. The grip tape 32 helps to prevent any bodily movement of the arm, hand and fingers of the user during the color application process. The applicator base is made of a sturdy material so as to support the weight of the henna applicator device. At each of the four corners of the applicator base, there is provided a rubber stopper 46. The rubber stopper will prevent the henna applicator device 12 from sliding on a surface/platform.

The henna applicator device 12 can be powered by means of battery and/or AC/DC current. For supplying the current to the henna applicator device 12, there is provided a power cord 42 with a connector plug 24. This connector plug 24 is connected to any power plug that can support the voltage required to operate henna applicator device 12.

An example of the method of enabling the present invention is described in detail with reference to FIG. 6 using henna as the coloring substance as per one embodiment of the invention.

Before the user starts applying henna on the arm using the present invention, the user loads the material holding material of the color applicator unit with the henna paste and closes it with the lid.

To prepare the henna paste, fresh henna leaves are ground to prepare fine powder. This powder is sieved to ensure the removal of large particles. The fine powder is then mixed with water to form a paste. Water can also be replaced by fresh or bottled lemon juice. As the more acidic the mixture, the better the color it imparts on the body surface. Sugar is then added to the paste. This will help the henna paste to stick to the body surface. Other ingredients may also be added to the henna paste to impart fragrance and health benefits to the user. These may be selected from a group comprising coffee, tea, tamarind, dried lime, cloves, essential oils like cajeput, tea tree, revensara, lavender and spices. The henna paste may be then stored for about 5-10 hrs at room temperature in an air tight container and used whenever necessary.

The user then switches on the device using the power button present on the touch screen display board and selects a design from the memory of the system 72. The user then places its arm on the applicator base over the grip tape. The system scans the arm of the user 74 using the scanning device and generates a 3D-image. The user is able to view the selected design relative to the arm image. The user may either choose to modify the selected design or change the orientation of the design based on his requirements or proceed with the color application process. The user then selects "start color application" on the touch screen display board. Then, the data processing unit will process the images and the design to determine the position coordinates of the scanning device and a color applicator unit on the axle assembly 76 after which the scanning device and the color applicator unit will be positioned on the axle assembly for henna application 78. The henna applicator device subsequently starts applying henna on the arm of the user 80.

If the user wishes to take a break during the color application process, the user may select "pause color application" from the touch screen display unit. This will pause the color application process. Once the user is ready, the user can select "continue color application" from the touch screen display unit to resume color application process.

As the system is capable of detecting movement of the arm of the user during the color application process, if during the color application process, the user moves the arm, the system will detect the movement and halt the color application process 84 and will resume to do so only after the user manually selects "continue color application" from the touch screen display unit.

The present invention is configured to apply the coloring substance starting from the arm and then move towards the hand and fingers.

The user after applying henna can switch on the fans by means of the rocker switch to dry the henna.

With the present invention, the user can obtain an accurate replica of the selected design on the arm, hand and fingers of the user.

Applications and Advantages

The present invention can be used to apply henna and any other coloring substance on the body surface with enhanced replication accuracy. The system is small and compact in nature and can be easily stored in cupboards, drawers and in any other small places. The device can be folded and thus ensures easy storage.

The material holding container has a capacity in the range of from about 20 ml to 50 ml of the coloring substance. This volume is sufficient to apply the coloring substance on a single side of the arm, hand and fingers during use. While applying the coloring substance on the other side of the arm, the material holding container is removed from its hoop, washed and refilled with the coloring substance for next usage. It is important to note that any residual coloring substance left in the color holding container is required to be washed clean before keeping the device away.

The system of the present invention is simple to use and can be used multiple times. This substantially reduces the cost of applying henna as there is only a one time investment of purchasing the system. During each application, the user may select designs and replicate them onto the body surface accurately consuming less time. Hence, this system finds its use in beauty salons, professional tattoo application centers, with henna professionals and is also suitable for domestic use.

The most important advantage of this present invention is the ability of the system to detect movements of the body surface during the color application process. As the system is capable of halting and resuming the color application process from the exact position where the color application process had halted, the user may take a break and resume the color application process as per its convenience.

The device further has the ability to enter into sleep or hibernation mode, a few minutes after the color application process is halted. The helps in reducing the power consumption of the device and reduce electricity bills.

The present invention can take the form of a computer program product comprising program modules accessible from computer-usable or computer-readable medium storing program code for use by or in connection with one or more computers, processors, or instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium (though propagation mediums in and of themselves as signal carriers are not included in the definition of physical computer-readable medium). Examples of a physical computer-readable medium include a semiconductor or solid state memory, magnetic tape, a removable computer diskette, a random access memory (RAM), a read-only memory (ROM), a rigid magnetic disk and an optical disk, Current examples of optical disks include compact disk—read only memory (CD-ROM), compact disk—read/write (CD-R/W) and DVD. Both processors and program code for implementing each aspect of the technology can be centralized or distributed (or a combination thereof) as known to those skilled in the art.

It is to be understood that the above described embodiments are merely illustrative of the numerous and varied other embodiments which may constitute applications of the techniques of the present invention. Such other embodiments may be readily devised by those skilled in the art without departing from scope of this present invention and it is our intent that they be deemed within the scope of our present invention.

What is claimed is:

1. A system for applying a coloring substance to form at least one design pattern on a body surface of a human, the system comprising:
   a scanning device operable to scan the body surface and generate a topographical profile thereof,
   a color applicator unit operable to apply the coloring substance to the body surface based on the design pattern,
   an axle assembly configured to permit movement of the scanning device and the color applicator unit relative thereto, and
   a controller configured to regulate an operation of the scanning device and the color applicator unit and halt the operation thereof based on a displacement of the body surface relative to the axle assembly.

2. The system according to claim 1, wherein the controller is configured to determine a first set of position coordinates of the color applicator unit relative to the axle assembly, wherein the first set of position coordinates are determined based on a first and a second set of reference coordinates corresponding to the design pattern and the topographical profile respectively, and to operate the color applicator unit to apply the coloring substance at the first set of position coordinates.

3. The system according to claim 1, wherein the scanning device is further configured to detect the displacement of the body surface relative to the axle assembly and provide corresponding information to the controller.

4. The system according to claim 1, wherein the controller halts the operation of the color applicator unit based on the displacement exceeding a predefined threshold value, wherein the threshold value is from about 0.15 mm to about 0.35 mm.

5. The system according to claim 1, wherein the controller resumes the operation of the scanning device and the color applicator unit based on receiving a corresponding user input, wherein the controller operates the scanning device to rescan the body surface to determine a second set of position coordinates of the color applicator unit relative to the axle assembly, wherein the second set of position coordinates are determined based on a first and a third set of reference coordinates corresponding to the design pattern and the topographical profile respectively, and further operates the color applicator unit to apply the coloring substance at the second set of position coordinates.

6. The system according to claim 5, wherein the controller is further configured to determine a starting position coordinate from within the second set of position coordinates corresponding to a halting position coordinate from within the first set of position coordinates, wherein the controller operates the color applicator unit starting from the starting position coordinate.

7. The system according to claim 1 further comprising a memory system configured for storing a plurality of design patterns; and a user interface configured to display the plurality of design patterns, and receive at least a first user input for selecting the at least one design pattern from the plurality of design patterns.

8. The system according to claim 7, wherein the memory system is configured to be communicatively coupled to an external storage medium and import one or more design patterns stored therein.

9. The system according to claim 7, wherein the user interface is further configured to receive at least a second user input to alter the at least one design pattern.

10. The system according to claim 1 further comprising means for blowing air over the body surface for enabling drying of the coloring substance applied thereto.

11. A method for operating a color application system for applying a coloring substance to form at least one design pattern on a body surface of a human, the color application system having a scanning device operable to perform a scanning operation, a color applicator unit operable to apply the coloring substance, and an axle assembly permitting movement of the scanning device and the color applicator unit relative thereto, the method comprising:
    operating the scanning device for scanning the body surface and generating a topographical profile thereof;
    operating the color applicator unit for applying the coloring substance to the body surface based on the design pattern; and
    halting an operation of the scanning device and the color applicator unit based on a displacement of the body surface relative to the axle assembly.

12. The method according to claim 11 further comprising determining a first set of position coordinates of the color applicator unit relative to the axle assembly, wherein the first set of position coordinates are determined based on a first and a second set of reference coordinates corresponding to the design pattern and the topographical profile respectively, and operating the color applicator unit to apply the coloring substance at the first set of position coordinates.

13. The method according to claim 11 further comprising operating the scanning device for detecting the displacement of the body surface relative to the axle assembly.

14. The method according to claim 11, wherein the operation of the scanning device and the color applicator unit is halted based on the displacement exceeding a predefined threshold value, wherein the threshold value is from about 0.15 mm to about 0.35 mm.

15. The method according to claim 11 further comprising resuming the operation of the scanning device and the color applicator unit based on receiving a corresponding user input, wherein the step of resuming the operation comprises rescanning the body surface to determine a second set of position coordinates of the color applicator unit relative to the axle assembly, wherein the second set of position coordinates are determined based on a first and a third set of reference coordinates corresponding to the design pattern and the topographical profile respectively, and operating the color applicator unit to apply the coloring substance at the second set of position coordinates.

16. The method according to claim 15 further comprising determining a starting position coordinate from within the second set of position coordinates corresponding to a halting position coordinate from within the first set of position coordinates, and operating the color applicator unit starting from the starting position coordinate.

17. The method according to claim 11 further comprising storing a plurality of design patterns in a memory system, displaying the plurality of design patterns through a user interface, and receiving at least a first user input through the user interface for selecting the at least one design pattern from the plurality of design patterns.

18. The method according to claim 17 further comprising communicatively coupling the memory system to an external storage medium and importing one or more design patterns stored therein into the memory system.

19. The method according to claim 17 further comprising receiving at least a second user input through the user interface for altering the at least one design pattern.

20. The method according to claim 11 further comprising blowing air over the body surface for enabling drying of the coloring substance applied thereto.

21. A computer program product embodied on a non-transitory computer readable medium, the non-transitory computer-readable medium comprising computer-executable instructions for operating a color application system for applying a coloring substance to form at least one design pattern on a body surface of a human, the color application system having a scanning device operable to perform a scanning operation, a color applicator unit operable to apply the coloring substance, and an axle assembly permitting movement of the scanning device and the color applicator unit relative thereto, the computer-executable instructions comprising:
    program instructions for operating the scanning device for scanning the body surface and generating a topographical profile thereof;
    program instructions for operating the color applicator unit for applying the coloring substance to the body surface based on the design pattern; and
    program instructions for halting an operation of the scanning device and the color applicator unit based on a displacement of the body surface relative to the axle assembly.

22. The computer program product according to claim 21 further comprising program instructions for determining a first set of position coordinates of the color applicator unit relative to the axle assembly, wherein the first set of position coordinates are determined based on a first and a second set of reference coordinates corresponding to the design pattern and the topographical profile respectively, and program instructions for operating the color applicator unit to apply the coloring substance at the first set of position coordinates.

23. The computer program product according to claim 21 further comprising program instructions for resuming the operation of the scanning device and the color applicator unit based on receiving a corresponding user input, wherein the program instructions for resuming the operation comprise program instructions for rescanning the body surface to determine a second set of position coordinates of the color applicator unit relative to the axle assembly, wherein the second set of position coordinates are determined based on a first and a third set of reference coordinates corresponding to the design pattern and the topographical profile respectively, and program instructions for operating the color applicator unit to apply the coloring substance at the second set of position coordinates.

24. The computer program product according to claim 23 further comprising program instructions for determining a starting position coordinate from within the second set of position coordinates corresponding to a halting position coordinate from within the first set of position coordinates, and program instructions for operating the color applicator unit starting from the starting position coordinate.

* * * * *